United States Patent [19]
Kane

[11] Patent Number: 6,132,642
[45] Date of Patent: Oct. 17, 2000

[54] METHOD OF PREPARING SMALL PARTICLE SIZE PHOSPHORS

[75] Inventor: James Kane, Lawrenceville, N.J.

[73] Assignee: Sarnoff Corporation, Princeton, N.J.

[21] Appl. No.: 08/270,089

[22] Filed: Jul. 1, 1994

[51] Int. Cl.$^7$ .................................................. C09K 11/84
[52] U.S. Cl. .................................................... 252/301.4 S
[58] Field of Search ...................... 232/301.4 S, 301.4 R

[56] References Cited

U.S. PATENT DOCUMENTS

| | | | |
|---|---|---|---|
| 3,418,246 | 12/1968 | Royce | 252/301.4 S |
| 3,502,590 | 3/1970 | Royce et al. | 353/301.4 |
| 3,541,022 | 11/1970 | Hewes | 252/301.4 S |
| 4,690,832 | 9/1987 | Yale | 252/301.4 S |
| 5,015,452 | 5/1991 | Matijevic | 252/301.4 R |
| 5,043,265 | 8/1991 | Tanke et al. | 435/6 |

OTHER PUBLICATIONS

Kanehisa et al, Formation Process of $Y_2O_2S:Eu^{+3}$ in a Preparation With Flux, Jap. Electro. Chem. Soc. Solid State Tech.,pp. 2023–2027, Aug. 1985.

Beverloo et al, Inorganic Phosphors as New Luminescent Labels for Immunocytochemistry and Time–Resolved Microscopy, Cytometry 11:784–92, 1990 no month.

Beverloo et al, "Preparation and Microscopic Visualization of Multicolor Luminescent Immunophosphors", Cytometry 11:661–670 (1992).

Beverloo et al, "A Comparison of the Detection Sensitivity of Lymphosyte Membrane Antigens Using Fluorescein and Phosphor Immunoconjugates", J. Histochemistry & Cytochemistry, 41 No. 5 )1993) pp. 719–725.

Beverloo et al, "Inorganic Phosphors as New Luminescent Labels for Immunocytochemistry and Time–Resolved Microscopy", Cytometry 11:784–792 (1990).

Kanehisa et al, Formation Process of $Y_2O_2S:Eu^{3+}$ in a Preparation with Flux, J. Electro Chem. Soc. Solid State Technol. Aug. 1985, pp.2023–2027.

Matijevic, Preparation and Properties of Uniform Size Colloids, Chem. Mater. 1993, 5, 412–426.

*Primary Examiner*—C. Melissa Koslow
*Attorney, Agent, or Firm*—William J. Burke

[57] ABSTRACT

A process for preparing phosphor particles having a particle size of 1 micron or less and that are spherical in shape. Such phosphors are useful, for example, as upconverter phosphors in labels for immunoassays. The process comprises preparing a dilute solution of soluble salts of the rare earth metals in amounts required to make the desired phosphor, adding a chemical agent that releases hydroxyl ions, precipitating small spherical particles of a rare earth hydroxycarbonate compound, heating the particles in oxygen at a limited temperature to form the corresponding trioxide particles, and heating the trioxide particles in a sulfur-containing flux in the absence of oxygen at a temperature no higher than about 900° C. to convert the trioxide particles to the corresponding oxysulfide phosphor particles.

16 Claims, 4 Drawing Sheets

METHOD OF PREPARING SMALL PARTICLE SIZE PHOSPHORS

This invention relates to improved phosphors having uniform, small, spherical particle size. More particularly, this invention relates to phosphors having uniform particle size below about 1 micron.

BACKGROUND OF THE INVENTION

Phosphors typically comprise one or more rare earth metals in a host material. Up-converter phosphors emit light in the visible wavelength radiation range (550–800 nanometers) when excited by long wavelength radiation, e.g., light in the infrared wavelength spectrum. This is accomplished by multiple absorption of infrared photons and energy transfer between the absorbing and emitting ions. For example, it is known that yttrium oxysulfide, $Y_2O_2S$, gadolinium oxysulfide, $Gd_2O_2S$, and lanthanum oxysulfide $La_2O_2S$, doped with certain activator couples, will be excited by 0.96 micron wavelength radiation. Such radiation can be provided by semiconductor lasers.

These phosphors have been tried as phosphorescent labels for biological assays. Detection methods for macromolecules such as proteins, drugs, polynucleotides and the like include an analytical reagent that binds to a specific target macromolecular species and produces a detectable signal, provided by a label, such as a radioisotope or covalently-linked fluorescent dye or phosphor. This process is shown in graphic form in FIG. 1, which shows attachment of a specific antigen to a microtiter plate surface, capture of an antibody by the antigen, and attachment of a phosphor label by the antigen/antibody. This attachment and the relative sizes of known phosphors and antibodies are further illustrated in FIG. 2.

Up-converting phosphors have several advantages over other known materials, such as radioisotopes and covalently-linked fluorescent dyes, for such label applications. Radioimmunoassays, while they are sensitive, use radioactive materials which are potential health hazards for the operators of the tests, and which in turn also require special handling and expensive disposal problems. Radioisotopes are unstable and they do not produce strong signals in the ultraviolet, infrared or visible portions of the electromagnetic spectrum, and thus cannot be used for methods including microscopy, image spectroscopy and flow cytometry that employ optical methods for detection of the label.

Fluorescent labels thus have come into widespread use for such methods, including small organic dye molecules which can be illuminated with light of a particular excitation frequency so that they give off emissions that can be detected by electro-optical sensors. However, these fluorescent dye labels have limited sensitivity because the specific fluorescent signal of the label is difficult to detect from nonspecific background fluorescent signals given off by other reagents required for the test, such as serum, fixatives and the sample itself, as well as autofluorescence in the visible wavelength range of optical lenses and excitation light reflected from the equipment used to carry out the test. As an example, whole blood samples strongly scatter light at short wavelengths of about 600 nm, which is also the emission range of fluorescent dye reporters. Thus such fluorescent dyes are not well suited for immunoassays of whole blood. Since fluorescent dyes have a short lifetime, about 1–100 nanoseconds, it is often difficult to measure the label light. Another disadvantage in the use of fluorescent dyes is that these dyes bleach out due to photolytic decomposition of the dye molecules during exposure to light.

The use of up-converting phosphors for immunoassays has been disclosed. Such phosphors can be excited by photons of a frequency which can be provided by inexpensive near-infrared laser diodes or light-emitting diodes for example, and they emit light of a lower frequency band, in the visible range. Thus the photons of the emitted radiation are of higher energy than the excitation energy, and the emitted radiation is "up-shifted" from the excitation radiation. Since background fluorescence in the visible range is negligible if near infrared excitation wavelength light is used, the use of up-converter labels provides an essentially background-free visible emission signal. The ability to use efficient laser diodes or light-emitting diodes (LEDs) reduces the system size, the power requirements and the costs required to perform the assay. Solid state diode lasers can be tailored to operate at any desired wavelength in the near infrared range, and since they are inexpensive they are compatible with a low cost assay kit.

The phosphors of the invention can be used as immunoassay labels by attaching them to one or more probes, such as antibodies, protein A, polypeptide ligands of cellular receptors, polynucleotides, drugs, antigens, toxins and the like. When they serve as a reporter, or a light detectable marker, attachment of the label can be accomplished in various known ways, for example by coating phosphor particles with a polycarboxylic acid whereby various probes will be physically adsorbed to the surface of the phosphor particles. Other attaching agents such as siloxanes are also well known.

Such phosphor particles are typically smaller than about 3 microns in diameter, but it is preferred that the phosphor particles be as small as possible while still generating a detectable signal. For particular tests, such as detection of an abundant nuclear antigen in a permeabilized cell, a small phosphor particle is required that can readily diffuse and penetrate subcellular structures. Further, since during the course of the assay bound and unbound phosphor particles must be separated and differentiated, it would be highly desirable that the phosphor particles be uniform in size. The size of the particles, their weight and their morphology are all important criteria because they affect the strength of particle binding and the specificity of the separation process. Further, since in an assay application each of the particles should have a like number of active binding sites, it is also desirable that the particles be of similar size.

Thus the as-formed phosphors are generally milled to reduce their particle size. Prior art milling methods employ milling in a conventional barrel mill with zirconia and/or alumina balls for up to 48 hours or longer. This produces phosphor particles of from 0.01 to 3 microns in size. If a particular particle size is desired, fractions of the desired particle size can be prepared by sedimentation which generally takes a day or more, and removal of the undesired (larger) particle sizes.

It is apparent that the milling and sedimentation processes are quite lengthy, which adds to the cost of preparing suitable phosphors for immunoassay labels. But more importantly, the milling process acts to fracture the large crystalline phosphor particles, forming irregularly shaped particles.

Thus, the milling process produces non-spherical particles and a quite large range of particle sizes, even after sedimentation. Thus it would be highly desirable to be able to produce phosphor particles having uniform, small particle size and spherical morphology.

Submicron particles of yttrium oxide have been made, doped with ytterbium and erbium $[(Y_{0.86}Yb_{0.08}Er_{0.06})_2O_3]$.

This is a relatively efficient red up-converter phosphor, but it is slightly water sensitive, especially as small particles. Thus, in order to produce a more efficient luminescent material, it is annealed in air at 1500° C. However, this annealing process forms aggregates of the phosphor, in which some of the particles grow together, and which are very difficult to break apart, even by sonication techniques. Further, when the oxide is converted to the corresponding oxysulfide for use as a phosphor label, the phosphor particles aggregate further and produce non-spherical particles of 1–3 microns or more in size.

Thus it would be highly desirable to be able to form yttrium or gadolinium oxysulfide phosphors having small uniform particle size wherein the particles are spherical.

SUMMARY OF THE INVENTION

We have found a process for making phosphors, including upconverter phosphors, having spherical particles less than 1 micron in size. In accordance with the present invention, a small, spherical particle size host hydroxycarbonate is first made by precipitation from dilute solution. The hydroxycarbonates are heated in air to form the corresponding oxides, under conditions that retain the shape and particle size of the hydroxycarbonate precursor. The oxides are then heated at a maximum temperature of about 900° C. in a non-oxidizing atmosphere in an alkali polysulfide flux to form the corresponding oxysulfide phosphors. The oxide particles do not appreciably aggregate or change their surface morphology during conversion to the oxysulfides, which are highly efficient up-converter phosphors.

The oxysulfide phosphors of the invention can also be made directly from the precursor hydroxycarbonates without increasing the particle size or changing the surface morphology of the hydroxycarbonate particles. Thus small, uniform particle size, spherical particles are obtained.

The present low temperature process heats the starting host material for the phosphor and the activator/emitter pair in a low temperature flux to a maximum temperature of about 900° C., which avoids the formation of aggregates, or produces aggregates that can be separated by sonication, to produce a highly efficient phosphor having uniform spherical particles of small particle size.

DETAILED DESCRIPTION

Figure 1:
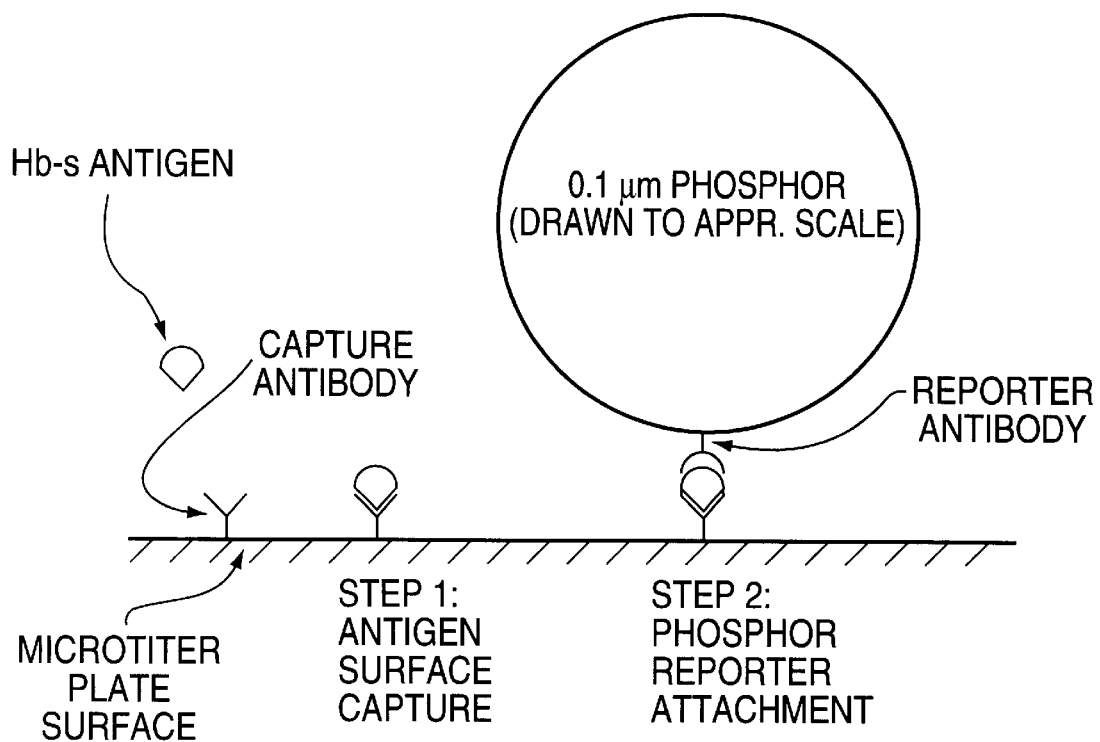
FIG. 1 is an illustration of the process of attaching phosphor labels to a reporter antibody during an immunoassay.
Figure 2:
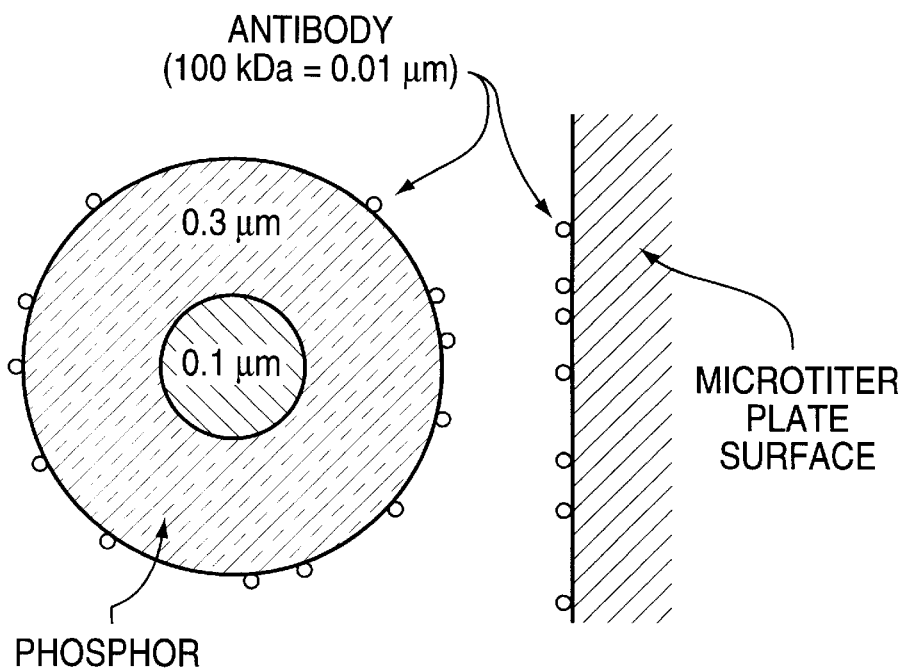
FIG. 2 is an illustration of the relative size of the phosphor label and an antibody.

The preferred phosphors of the invention include upconverter oxysulfides such as yttrium oxysulfides and gadolinium oxysulfides, containing various known activator/emitter couples. Other oxysulfides can also be used, such as lutetium oxysulfides. Suitable activator couples include ytterbium/erbium, ytterbium/thulium and ytterbium/holmium. By combination of the oxysulfides and the activator couples, red, blue or green phosphors can be made. Generally the absorber is ytterbium and the emitter is erbium, holmium, terbium or thulium, although the invention is not limited to these materials. The molar ratio of absorber: emitting center is generally at least about 1:1, but can be higher, up to about 2500:1; however, the ratio used is generally about 25:1 to about 50:1. The ratio will be selected on the basis of various properties of the resultant phosphor, including chemical properties, manufacturing efficiency, absorption cross-section, excitation and emission wavelengths, quantum efficiency and the like. The ratio chosen will also generally depend upon the particular absorber-emitter couple employed.

For example, to form an efficient phosphor, the absorber: emitter ratio for Yb:Er couples is generally about 20:1 to about 100:1, whereas the absorber: emitter ratio for Yb:Tm and Yb:Ho couples is typically in the range of about 500:1 to about 2000:1. Up-converting phosphors may conveniently comprise about 10–30% of Yb and either 1–2% Er, about 0.1–0.05% Ho, or about 0.1–0.05% Tm, although the present invention is not so limited.

Examples of suitable phosphors for use as immunoassay labels include phosphors having the formula $Y_xYb_yEr_z$ wherein x is 0.7–0.9 and each of y and z is 0.05–0.12. This is a green-emitting phosphor. Gadolinium oxysulfides containing ytterbium and holmium as the absorber/emitter couple is also a green phosphor. Gadolinium oxysulfide doped with ytterbium/thulium as the absorber/emitter couple is a blue-emitting phosphor. When small particle size phosphors are employed, an increase in the doping levels of activator/emitter couples may be desirable to increase the quantum conversion efficiency of the phosphor.

Various processes of making oxysulfide phosphors are well known to one skilled in the art, but they do not produce small spherical particles of the desired particle size without the need for milling.

In accordance with the present process, a mixture of a rare earth water-soluble salt, such as the nitrate, together with the water-soluble salts of an activator/emitter couple, in the molar proportion of the phosphor to be made, is dissolved in water so as to make a dilute solution. A concentrated aqueous solution can be prepared first, which can be further diluted.

An chemical agent that slowly hydrolyses in water, releasing hydroxyl ions, such as urea, is then added to the rare earth solution. Urea slowly decomposes in water, shifting the pH in a slow, controllable fashion. The solution is digested for some period of time until the rare earth hydroxycarbonate precipitates, visible as a cloudiness in the solution. The resultant particles are very small, i.e., less than one micron, spherical particles. This reaction can be continued until the supply of rare earths in solution has been depleted.

Suitably, the rare earths used are gadolinium or yttrium which can contain activator/emitter couples of ytterbium together with erbium, thulium, lutetium or holmium and the like as discussed above.

The hydroxycarbonate particles are collected, as by centrifugation, and then fired in an oxygen-containing atmosphere to convert the hydroxycarbonate to the corresponding oxide. The firing temperature is very important. In order to maintain the small particle size of the hydroxycarbonate precipitates, the firing temperature must be maintained in the range of about 700 to about 1000° C. A preferred temperature is about 700° C. At higher temperatures, aggregates and irregularly shaped particles form due to grain growth, and the desired spherical morphology will not be maintained.

Since the rare earth oxides are not highly efficient phosphors, the oxides are then converted to the oxysulfides which are more efficient phosphors.

The conversion of phosphors from their oxides to their oxysulfides is known and described in U.S. Pat. No. 3,502,590 to Royce et al, incorporated herein by reference. The rare earth oxides are heated in a suitable alkali polysulfide flux composition in the absence of oxygen to form the corresponding oxysulfide. Suitable fluxes include sulfur and a mixture of alkali metal carbonates, phosphates or sulfates.

The rare earth oxide particles and flux are packed into a closed alumina crucible and heated to firing temperature. The crucible can be contained within another crucible, packed in charcoal, etc. to keep oxygen out of the system during firing. Again, the firing temperature is very important in order to maintain the particle size and morphology of the oxide during conversion to the oxysulfide compound. Too high a firing temperature results in a change in both the size and shape of the oxysulfide particles, leading to an increase in size and formation of non-spherical particles, and to the formation of aggregates. Too low a firing temperature however, will not form the oxysulfide. Generally a minimum temperature of about 600° C. is required for reaction to occur rapidly and completely. However, we have found that a maximum temperature of about 900° C. is necessary to give high luminescent efficiency in the phosphor, yet maintain the size and morphology of the original oxide particles. The firing time is also important. Firing is continued until substantially all of the rare earth oxide has been converted to the oxysulfide phosphor compound. During this firing step the activator couple ions are incorporated into the oxysulfide crystal which is generally complete after about 30 minutes.

Thus the above process results in formation of rare earth oxysulfide up-converting phosphors having small, uniform particle size and spherically shaped particles useful as labels for immunoassays. These particles can be made less than one micron in size, and thus do not require milling or separation of particle sizes.

In order to form stable suspensions of the small spherical phosphor particles for use as an immunoassay label, the phosphor particles can be coated or treated with a surface active agent, as with a polycarboxylic acid. This produces a stable aqueous suspension of the phosphor particles, typically at a pH of 6–8. Since phosphors are sensitive to acid solutions, a buffer can also be added to ensure that proper pH is maintained. In the case of oxysulfide phosphors, the phosphor particles also can be dispersed in a polar solvent, such as acetone or DMSO and the like, to generate a monodisperse emulsion for a stock solution, which can be further diluted into an aqueous solution such as buffered saline.

The invention will be further described in the following examples, but the invention is not meant to be limited to the details described therein. In the examples, all references to water refer to filtered, distilled water.

EXAMPLE 1

Part A. Preparation of Oxide Phosphor

A solution of yttrium, ytterbium and erbium solutions as their nitrates in proportion so as to produce $Y_{0.86}Yb_{0.08}Er_{0.06}O_2S$ was made. An aliquot of this solution containing 0.1 mol of the mixed oxide was added to a 5 liter container. The solution was diluted to 3.5 liters with water.

70 Grams of urea dissolved in 0.5 liter of water was added and the solution heated to boiling for several hours, when the rare earth hydroxy carbonate precipitated out. The reaction was continued until the solution was depleted of rare earth metals.

The precipitate was collected and centrifuged, washed, dried and fired in air at 700° C. to convert the hydroxycarbonate to the corresponding oxide.

Figure 3:
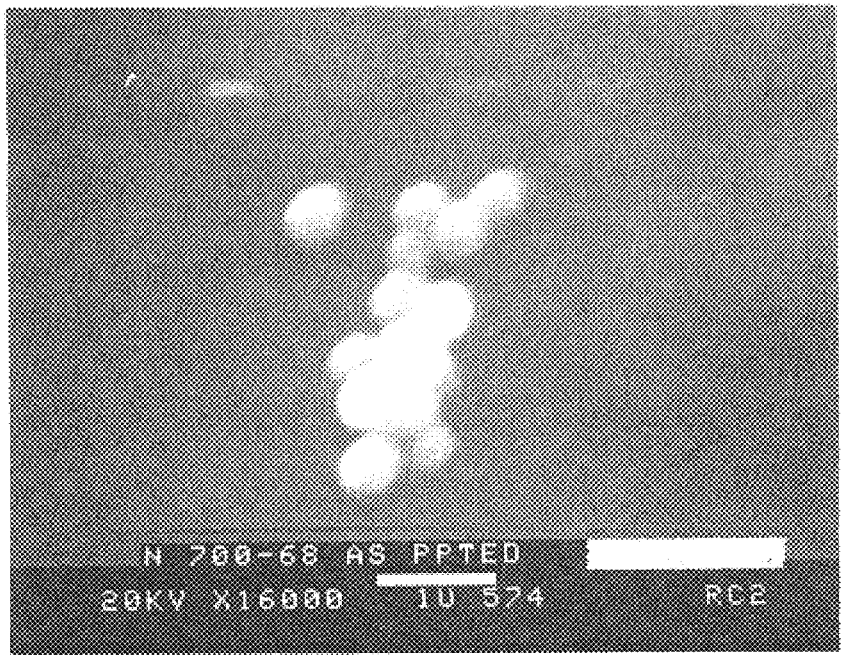
FIG. 3 is a photomicrograph of yttrium hydroxycarbonate particles as precipitated from solution.

Photomicrographs of the hydroxycarbonate and corresponding oxide materials were taken. FIG. 3 is a photomicrograph of the hydroxycarbonate as precipitated at 8000× magnification. It is apparent that the precipitated particles are small, almost perfectly spherical particles.

Figure 4:
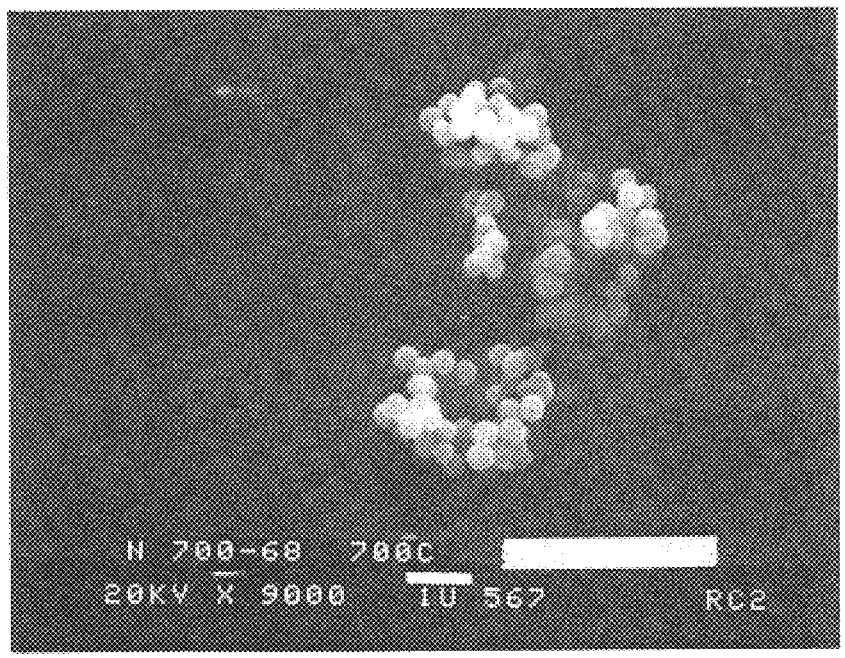
FIG. 4 is a photomicrograph of yttrium oxide phosphor particles after firing at 700° C.

FIG. 4 is a photomicrograph of the corresponding oxide formed after heating at 700° C. for 2 hours, taken at 9000× magnification. It is apparent that the particles are still small, spherical particles.

Part B. Preparation of Oxysulfide Phosphor

The oxides were then converted to the highly efficient oxysulfide phosphor using a polysulfide flux in a non-oxidizing atmosphere and firing at a temperature of no more than 900° C.

Twenty-five grams of the mixed oxide, 8.0 grams of sulfur, 1.0 gram of potassium sulfate, 3.0 grams of lithium sulfate and 10.5 grams of potassium carbonate were milled together and fired in a capped alumina crucible in a charcoal pack.

After firing for three hours, the polysulfide flux was removed by washing with water, and a final rinse with dilute nitric acid solution to ensure complete removal of the polysulfide and other salts.

The phosphor was sonified to break up any particulate aggregates, centrifuged and dried.

Figure 5:
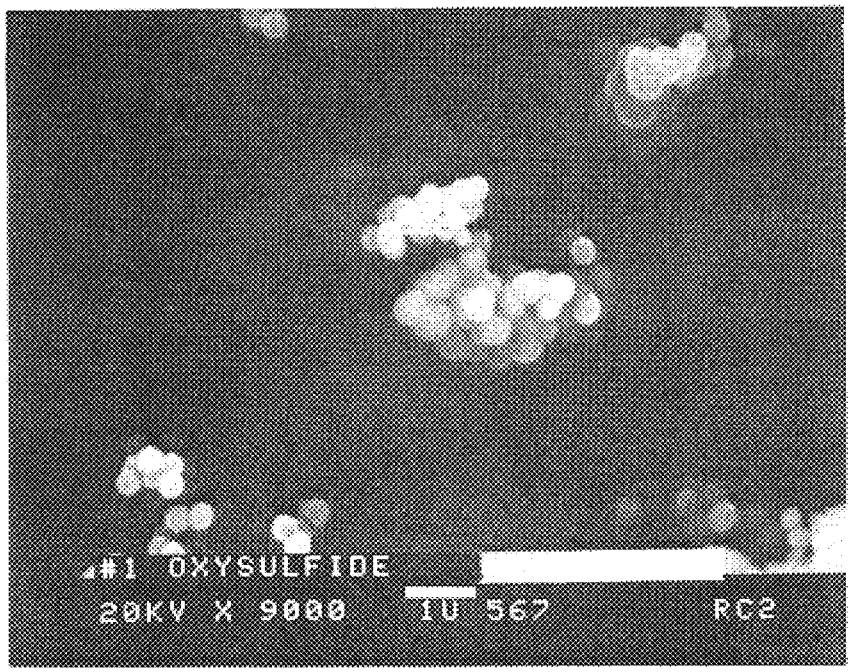
FIG. 5 is a photomicrograph of yttrium oxysulfide phosphor particles after firing at 900° C. in a polysulfide flux.

FIG. 5 is a photomicrograph of the oxysulfide having a particle size of 0.4 micron. It can be seen that the particles are little changed in morphology from the corresponding oxide.

COMPARATIVE EXAMPLE 1

The procedure of Example 1 Part A was repeated, except that the hydroxycarbonate particles were heated at 1350° C. for three hours.

Figure 6:
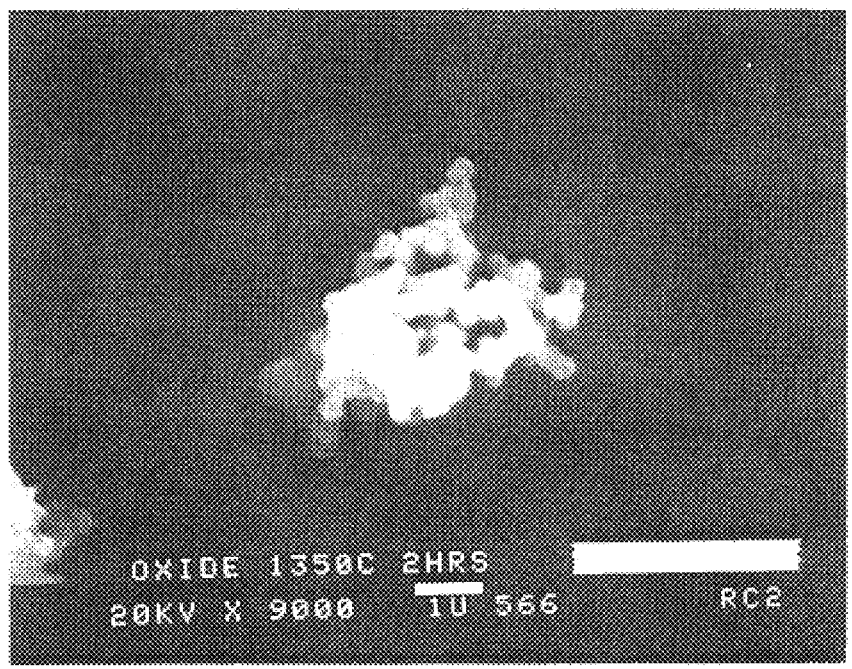
FIG. 6 is a photomicrograph of yttrium oxide phosphor particles heated at 1350° C. for two hours.

FIG. 6 is a photomicrograph of the corresponding oxide at 9000× magnification. It is apparent that the particles have coalesced into large aggregates and the individual particles are no longer spherical, but crystal faceting has occurred.

COMPARATIVE EXAMPLE 2

Figure 7:
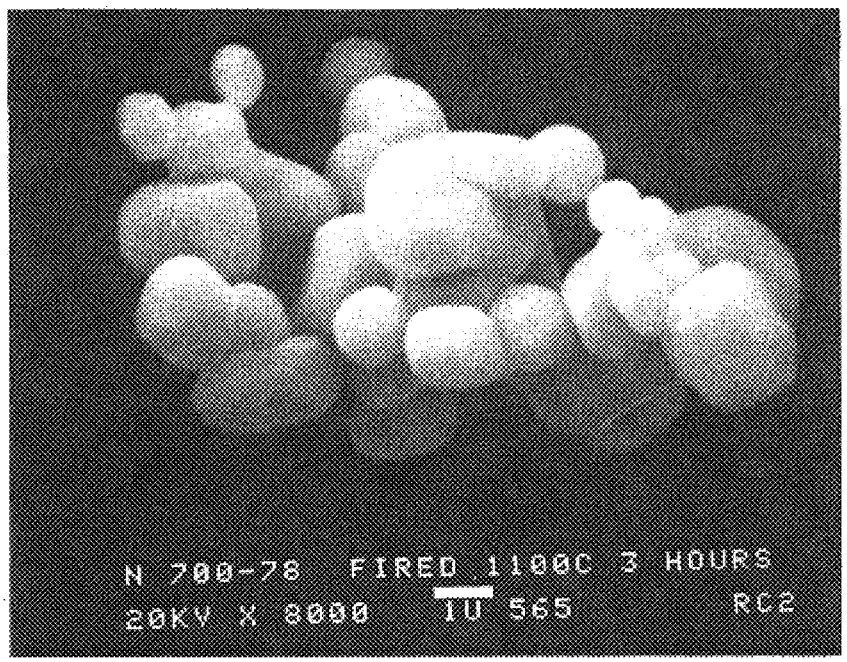
FIG. 7 is a photomicrograph of yttrium oxysulfide phosphor particles after firing at 1100° C. for three hours.

The procedure of Example 1 Part B was repeated, except that the oxide was heated at 1100° C. for three hours. FIG. 7 is a photomicrograph of the corresponding oxide at 8000× magnification. This produces a highly efficient luminescent phosphor but it is apparent that the individual particles are much bigger than the oxide starting material, and they are no longer spherical.

Although the invention has been described in terms of specific embodiments, the invention is not meant to be limited to the details therein, but is to be limited only by the scope of the attached claims. Various changes in the composition of the phosphors, the relative amounts of activator/ emitter couple ions, the composition of the solutions and fluxes herein described and reaction conditions can be substituted as will be known to one skilled in the art and are meant to be included. It is understood that the invention also includes singly activate up-converter phosphors such as erbium activated oxysulphides such as yttrium oxysulphide. The invention also includes the process of making down-converter phosphors, for example, ultraviolet stimulated phosphors such as europium or erbium doped oxysulphides such as yttrium or gadolinium oxysulphide manufactured. The invention also includes the process of making cathodo-luminescent phosphors, for example, europium or terbium doped oxysulphides such as yttrium or gadolinium oxysulphide.

I claim:

1. A process for the preparation of small particle size spherical phosphor particles which comprises:

a) preparing an aqueous solution of soluble salts of a rare earth phosphor-precursor metal in amounts required to make a phosphor and an organic chemical that releases hydroxyl ions by hydrolysis;

b) precipitating rare earth hydroxycarbonate particles from said solution, said particles having a spherical shape and particle size of less than one micron;

c) collecting the rare earth hydroxycarbonate particles;

d) heating the hydroxycarbonate particles in an oxygen-containing atmosphere at a temperature in the range of about 700 to about 1000° C. to form the corresponding rare earth oxide compound while maintaining the particle size and spherical shape of the hydroxycarbonate particles; and e) heating the rare earth oxide particles in a flux composition of sulfur and one or more salts selected from the group consisting of alkali metal sulfates, phosphates and carbonates in the absence of oxygen at a temperature of no more than about 900° C. to convert the oxide to the corresponding oxysulfide compound without changing the shape or the particle size of the particles.

2. The process of claim 1 wherein said aqueous solution of soluble salts comprises a dilute aqueous solution of soluble salts of a rare earth phosphor precursor and an activator/emitter rare earth pair suitable for making said phosphor in amounts which provide said phosphor and a chemical that releases hydroxyl ions by hydrolysis.

3. The process of claim 2 wherein the rare earth is gadolinium or yttrium.

4. The process of claim 3 wherein the activator couple is ytterbium and a member selected from the group consisting of erbium, holmium, terbium and thulium.

5. The process of claim 4 wherein the activator couple is ytterbium and erbium.

6. The process of claim 5 wherein the phosphor is $Y_{0.86}Yb_{0.08}Er_{0.06}O_2S$.

7. The process of claim 1 wherein the flux composition of step e) comprises a mixture of sulfur, potassium sulfate, lithium sulfate and potassium carbonate.

8. The process of claim 1 wherein the oxysulfide phosphor is collected, washed free of flux and treated with an agent so that the phosphor will form a stable suspension.

9. A stable aqueous suspension of the particles of claim 8.

10. An suspension according to claim 9 additionally containing a pH buffer so as to maintain the pH at from about pH 6–8.

11. A process for the preparation of small particle size spherical phosphor particles which comprises:

a) preparing an aqueous solution of soluble salts of a rare earth phosphor precursor and an activator/emitter rare earth pair in amounts which provide said phosphor and an organic chemical that releases hydroxy ions by hydrolysis;

b) precipitating rare earth hydroxycarbonate particles from said solution, said particles having a spherical shape and particle size of less than one micron;

c) collecting the rare earth hydroxycarbonate particles;

d) heating the hydroxycarbonate particles in an oxygen-containing atmosphere at a temperature in the range of about 700 to about 1000° C. to form the corresponding rare earth oxide compound while maintaining the particle size and spherical shape of the hydroxycarbonate particles; and e) heating the rare earth oxide particles in a flux composition of sulfur and one or more salts selected from the group consisting of alkali metal sulfates, phosphates and carbonates in the absence of oxygen at a temperature of no more than about 900° C. until the oxide has been converted to the corresponding oxysulfide compound, and washing the oxysulfide to remove the flux composition.

12. The process of claim 11 wherein the rare earth is gadolinium or yttrium.

13. The process of claim 12 wherein the activator couple is ytterbium and a member selected from the group consisting of erbium, holmium, terbium and thulium.

14. The process of claim 13 wherein the activator couple is ytterbium and erbium.

15. The process of claim 14 wherein the phosphor is $Y_{0.86}Yb_{0.08}Er_{0.06}O_2S$.

16. The process of claim 11 wherein the flux composition of step e) comprises a mixture of sulfur, potassium sulfate, lithium sulfate and potassium carbonate.

* * * * *